United States Patent [19]

Ravichandran et al.

[11] Patent Number: 4,668,727

[45] Date of Patent: May 26, 1987

[54] ESTER SUBSTITUTED BENZYLHYDROXYLAMINES AND STABILIZED POLYOLEFIN COMPOSITIONS

[75] Inventors: Ramanathan Ravichandran, Yonkers; Thomas E. Snead, Croton-on-Hudson, both of N.Y.

[73] Assignee: Ciba-Geigy Corporation, Ardsley, N.Y.

[21] Appl. No.: 800,626

[22] Filed: Nov. 21, 1985

[51] Int. Cl.[4] .......................... C07C 83/08; C08K 5/32
[52] U.S. Cl. .................................... 524/239; 524/240; 560/42; 562/444; 562/448
[58] Field of Search .................. 560/42; 562/444, 448; 524/239, 240

[56] References Cited

U.S. PATENT DOCUMENTS

| | | |
|---|---|---|
| 3,408,422 | 10/1968 | May . |
| 3,432,578 | 3/1969 | Martin . |
| 3,644,278 | 2/1972 | Klemchuk . |
| 3,778,464 | 12/1973 | Klemchuk . |
| 3,886,115 | 5/1975 | Murayama et al. ............... 524/206 |
| 3,926,909 | 12/1975 | Wei . |
| 4,242,224 | 12/1980 | Dean et al. . |
| 4,316,996 | 2/1982 | Collonge et al. . |
| 4,386,224 | 5/1983 | Deetman . |

Primary Examiner—Veronica P. Hoke
Attorney, Agent, or Firm—Luther A. R. Hall

[57] ABSTRACT

Ester substituted benzylhydroxylamine derivatives are effective in stabilizing polyolefin compositions containing a stabilizer or mixture of stabilizers selected from the group consisting of the phenolic antioxidants, the hindered amine light stabilizers, the alkylated hydroxybenzoate light stabilizers, the ultraviolet light absorbers, the organic phosphorus compounds, the alkaline metal salts of fatty acids and the thiosynergists, against degradation upon high temperature extrusion, exposure to the combustion products of natural gas, gamma irradiation or upon storage for extended periods. These ester substituted benzylhydroxylamine derivatives exhibit resistance to loss or extraction during processing and in end-use applications.

23 Claims, No Drawings

ESTER SUBSTITUTED BENZYLHYDROXYLAMINES AND STABILIZED POLYOLEFIN COMPOSITIONS

BACKGROUND OF THE INVENTION

The present invention pertains to polyolefin compositions containing a stabilizer or mixture of stabilizers selected from the group consisting of the phenolic antioxidants, the hindered amine light stabilizers, the alkylated hydroxybenzoate light stabilizers, the ultraviolet light absorbers, the organic phosphorus compounds, the alkaline metal salts of fatty acids and the thiosynergists, which are stabilized against degradation and/or discoloration by an effective amount of an ester substituted benzylhydroxylamine derivative.

The present invention also pertains to novel ester substituted benzylhydroxylamines.

Although phenolic antioxidants have long been known to be very effective stabilizers for polyolefins and have enjoyed wide commercial success for that use, polyolefin compositions stabilized with phenolic antioxidants tend to discolor upon heating at elevated temperatures for prolonged periods or upon exposure to the combustion products of natural gas.

While the concomitant addition of organic phosphites to such polyolefin compositions mitigates the discoloration, it remains a serious practical problem.

Likewise polyolefin compositions containing certain phenolic antioxidants and hindered amine light stabilizers tend to discolor upon storage for extended periods even at ambient temperatures.

The organic hydroxylamine compounds, such as N,N-dibenzylhydroxylamine, are generally known and some are commercially available.

U.S. Pat. Nos. 3,644,278 and 3,778,464 describe the use of substituted hydroxylamines of varying structures as antioxidant stabilizers for hydrocarbons including polyolefins. The use of such substituted hydroxylamines in polyolefins in combination with a phenolic antioxidant or in combination with an organic phosphorus compound, an ultraviolet light absorber, a thiosynergist or a hindered amine light stabilizer with the resulting resistance to degradation and/or discoloration is not disclosed or suggested.

U.S. Pat. No. 3,408,422 discloses the use of selected hydroxylamine derivatives in unsaturated polyester compositions to prevent premature gelation on storage.

U.S. Pat. No. 3,926,909 describes the use of substituted hydroxylamines as stabilizers to prevent the discoloration of polyurethanes (Spandex) upon exposure to light, smog or gas fumes.

U.S. Pat. No. 4,242,224 discloses that the pink discoloration which occurs in the amine antioxidant and antiozonant emulsions used in the latex industry at high pH values can be prevented or retarded by the use of dialkylhydroxylamine or mercaptan stabilizers.

U.S. Pat. No. 4,316,996 pertains to a process of preparing phenolic antioxidants in the presence of a hydroxylamine derivative and of a substituted oxime to yield a phenolic antioxidant which itself exhibits improved color and color stability. It is stated that, when such antioxidants are incorporated into rubber, the amount and rate of discoloration is reduced. The instant compositions are not disclosed or suggested.

U.S. Pat. No. 3,432,578 relates to conjugated diene polymer compositions stabilized against the adverse effects of ultraviolet light by use of diaryl or diaralkyl hydroxylamine compounds including N,N-dibenzylhydroxylamine. It is noted that the dialkylhydroxylamines are completely ineffective in stabilizing such polymer compositions. This patent mentions that other stabilizers may be used in conjunction with the hydroxylamine derivative and in Table I discloses stabilized compositions consisting of a conjugated diene polymer, phenolic antioxidants and N,N-dibenzylhydroxylamine. Such compositions were resistant to decomposition upon ultraviolet exposure.

U.S. Pat. No. 4,386,224 discloses the use of N,N-diethylhydroxylamine as a color stabilizer for monoalkyl phenols such as nonyl or dodecyl phenol.

OBJECTS OF THE INVENTION

A primary object of the instant invention is to provide novel ester substituted benzylhydroxylamines which are effective stabilizers for polyolefins and other substrates subject to oxidative, thermal or light-induced degradation.

The broad object of the instant invention is to provide a polyolefin or other polymer composition, stabilized against degradation, which contains a stabilizer or mixture of stabilizers selected from the group consisting of the phenolic antioxidants, the hindered amine light stabilizers, the alkylated hydroxybenzoate light stabilizers, the ultraviolet light absorbers, the organic phosphorus compounds and the thiosynergists, which also contain a hydroxylamine derivative.

An object of the present invention is to provide a stabilized polyolefin composition containing a phenolic antioxidant which is stabilized against discoloration upon exposure to heating or to the combustion products of natural gas by the concomitant presence of a hydroxylamine derivative.

Still another object of the present invention is to provide a stabilized polyolefin composition containing an alkaline metal salt of a fatty acid or said metal salt and a phenolic antioxidant which is stabilized against discoloration upon exposure to heating or to the combustion products of natural gas by the concomitant presence of a hydroxylamine derivative.

Another object of the instant invention is to provide ester substituted benzylhydroxylamines which are resistant to extraction or loss during processing and in end-use applications.

DETAILED DISCLOSURE

The instant invention pertains to compounds of formula I

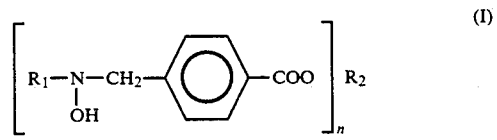

wherein
n is 1, 2, 3 or 4,
$R_1$ is alkyl of 1 to 36 carbon atoms, cycloalkyl of 5 to 12 carbon atoms, aralkyl of 7 to 9 carbon atoms or said aralkyl substituted by alkyl of 1 to 36 carbon atoms or by —$COOT_1$ where $T_1$ has the same meaning as $R_1$ or is hydrogen, or an alkali metal or ammonium salt,
when n is 1, $R_2$ has the same meaning as $R_1$ or is hydrogen, or an alkali metal or ammonium salt, when n is 2, R₂ is alkylene of 2 to 12 carbon atoms, cycloalkylene of 6 to 10 carbon atoms, arylene of 6 to 10 carbon atoms, alkylenearylenealkylene of 8 to 10 carbon atoms, or

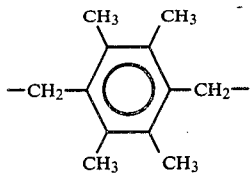

or R₂ is an alkaline earth salt, when n is 3, R₂ is alkanetriyl of 3 to 6 carbon atoms, or

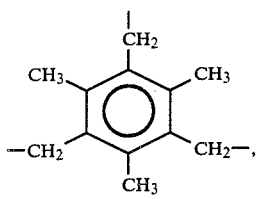

or when n is 4, R₂ is alkanetetrayl of 4 to 6 carbon atoms.

R₁ may be straight or branched chain alkyl of 1 to 36 carbon atoms such as methyl, ethyl, isopropyl, isobutyl, tert-butyl, n-octyl, 2-ethylhexyl, nonyl, n-dodecyl, n-octadecyl, eicosyl, tetracosyl, tricontyl or hexatricontyl, Preferably R₁ is alkyl of 1 to 18 carbon atoms.

R₁ may also be cycloalkyl of 5 to 12 carbon atoms such as cyclopentyl, cyclohexyl, cyclooctyl or cyclododecyl. Preferably R₁ is cyclohexyl or cyclododecyl.

R₁ is also aralkyl of 7 to 9 carbon atoms such as benzyl, alpha-methylbenzyl, or alpha,alpha-dimethylbenzyl where the benzyl group may additionally be substituted by alkyl, preferably methyl.

When T₁ or R₁ is an alkali metal salt, it may be for example sodium, potassium or lithium, preferably sodium or potassium.

Preferably R₁ is benzyl or benzyl substituted by —COOT₁.

In formula I, n is 1, 2, 3 or 4.

When n is 2, R₂ is alkylene of 2 to 12 carbon atoms such as ethylene, 1,2-propylene, trimethylene, tetramethylene, hexamethylene, octamethylene or dodecamethylene. Preferably R₂ is alkylene of 2 to 8 carbon atoms.

R₂ is also cycloalkylene of 6 to 10 carbon atoms such as cyclohexylene, preferably 1,4-cyclohexylene, or decahydronaphthylene.

R₂ can also be arylene of 6 to 10 carbon atoms such as o-, m- or p-phenylene, preferably m- or p-phenylene, or 1,4-naphthylene.

R₂ is also alkylenearylenealkylene of 8 to 10 carbon atoms, such as p-xylylene or ethylene-p-phenyleneethylene. Preferably R₂ is o-xylylene or

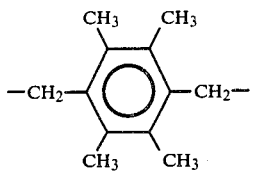

R₂ is also an alkaline earth salt, such as magnesium, calcium, strontium or barium, preferably magnesium or calcium.

When n is 3, R₂ is alkanetriyl of 3 to 6 carbon atoms such as glyceryl; or preferably

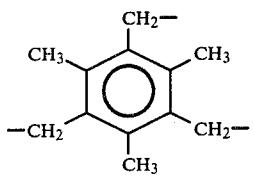

When n is 4, R₂ is alkanetetrayl of 4 to 6 carbon atoms, such as (—CH₂)₂C(CH₂—)₂ or 1,2,3,4-butanetetrayl.

The instant hydroxylamine may generally be prepared by reacting hydroxylamine or a substituted hydroxylamine with an activated halogen compound in the presence of an acid acceptor.

When the instant hydroxylamine derivative is a free acid (where T₁ or R₁ is hydrogen), it is prepared by the alkaline saponification of the corresponding lower alkyl ester followed by acidification to the free acid.

The corresponding alkali metal, alkaline earth or ammonium salt can be prepared from the free acid directly by neutralization with the appropriate hydroxide, or from the corresponding lower alkyl ester by a metathesis reaction with an alkali metal trimethyl silanoate.

The intermediate hydroxylamines, halogen compounds and amines are largely items of commerce or can be prepared by known methods.

The compounds of formula I are effective stabilizers in a wide range of organic substrates. Polymers which can be stabilized include:

1. Polymers which are derived from mono- or diolefins, e.g. polyethylene which optionally be crosslinked, polypropylene, polyisobutylene, polybutene-1, polymethylpentene-1, polyisoprene or polybutadiene, as well a polymers of cycloolefins, for instance of cyclopentene or norbornene.

2. Mixtures of the polymers mentioned under (1), for example mixtures of polypropylene with polyisobutylene.

3. Copolymers of the monomers based on the homopolymers cited under (1), for example ethylene/propylene copolymers, propylene/butene-1, copolymers, propylene/isobutylene copolymers, ethylene/butene-1 copolymers as well as terpolymers of ethylene and propylene with a diene, for example hexadiene, dicyclopentadiene or ethylidene norbornene, and copolymers of alpha-olefins, e.g., ethylene with acrylic or methacrylic acid.

4. Polystyrene.

5. Copolymers of styrene and of alpha-methylstyrene for example styrene/butadiene copolymers, styrene/acrylonitrile copolymers, styrene/acrylonitrile/-methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from $\alpha, \beta$-unsaturated acids and derivatives thereof, such as polyacrylates and polymethacrylates, polyacrylic amides and polyacrylonitrile.

9. Copolymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and and/or from aminocarboxylic acids or the corresponding lactams, for example polyamide 6, polyamide 6/6, polyamide 6/10, polyamide 11, polyamide 12, poly-m-phenyleneisophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic said resins and mixtures thereof with melamine/formaldehyde resins.

21. Unsaturated polyester resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the celluloe ethers, for example methyl cellulose.

The stabilizing of polyolefins, styrene polymers and polyamides and of polyurethanes is of particular importance, and the instant copolymers ae outstandingly suitable for this. Examples of such polymers are high density and low density polyethylene, polypropylene, ethylene/propylene copolymers, polystyrene, styrene/butadiene/acrylonitrile terpolymers, mixtures of polyolefins or of styrene polymers, and polyurethanes based on polyethers or polyesters, in the form of lacquers, filaments, films, sheets elastomers or foams.

The instant compounds of formula I are particularly effective in stabilizing material subject to oxidative, thermal or light-induced degradation where said material is selected from the group consisting of acrylonitrile-butadiene-styrene (ABS) resins, impact polystyrene, poly(phenylene oxide), polybutadiene, polyisoprene, natural rubber and lubricating oils.

The instant stabilizers are added to the plastics or oil in a concentration of 0.05 to 5% by weight, calculated relative to the material to be stabilized. Preferably, 0.1 to 2.5% by weight of the stabilizer calculated relative to the material to be stabilized, is incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The stabilizers can also be added to the plastics to be stabilized in the form of a master batch which contains these compounds, for example in a concentration of 2.5 to 25% by weight.

Although the compounds of the invention may be used to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.05 to about 5% by weight of the stabilized composition, although this will vary with the particular substrate and application. An advantageous range is from about 0.1 to about 2.5%.

The stabilizers of formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.05 to about 5%, preferably from about 0.1 to about 2.5% by weight of various conventional additives, such as the following, particularly phenolic antioxidants or light-stabilizers, or mixtures thereof:

1. Antioxidants 1.1. Simple 2,6-dialkylphenols, such as, for example, 2,6-di-tert.-butyl-4-methylphenol, 2-tert.-butyl-4,6- dimethylphenol, 2,6di-tert.-butyl-4-methoxymethylphenol and 2,6-dioctadecyl-4-methylphenol.

1.2. Derivatives of alkylated hydroquinones, such as for example 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl)adipate.

1.3. Hydroxylated thiodiphenyl ethers, such as for example 2,2'-thio-bis-(6-tert.-butyl-4-methylphenol), 2,2'-thio-bis-(4-octylphenol), 4,4'-thio-bis-tert.butyl-3-methylphenol), 4,4'-thio-bis-(3,6-di-sec.-amylphenol), 4,4'-thio-bis-(6-tert.-butyl-2-methylphenol) and 4,4'-bis-(b 2,6-dimethyl-4-hydroxy-phenyl)disulfide.

1.4. Alkylidene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol),4,4'-methylene-bis-(2,6-tert.butyl-phenol) 2,6-di-(3-tert.butyl-5-methyl-2-hydroxybenzyl)-4-methylphenol 2,2'-methylene-bis-[4-methyl-6-(α-methylcyclo-hexyl)-phenol], 1,1-bis(3,5-dimethyl-2-hydroxyphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5. O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6. Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7. Hydroxybenzyl-aromatic compounds, such as, for example, 1,3,5-tri-(3,5-di-tert.-butyl-4-hydroxybenzyl)-2,4,6-trimethyl-benzene, 1,4-di-(3,5-di-tert.-butyl-4-hydroxybenzyl)-2,3,5,6-tetramethylbenzene and 2,4,6-tri-(3,5-di-tert.-butyl-4-hydroxy-benzyl)-phenol.

1.8. s-Triazine compounds, such as, for example 2,4-bis-octylmercapto-6-(3,5-di-tert.-butyl-4-hydroxy-anilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenyl)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

1.9. Amides of β-(3,5-di-tert.-butyl-4-hydroxyphenyl)-propionic acids, such as, for example 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine, N,N'-bis-β-(3,5di-t-butyl-4-hydroxyphenyl)-propionyl-hydrazine.

1.10. Esters of β-(3,5-di-tert.-butyl-4-hydroxyphenyl)-propionic acid with monohydric or polyhydric alcohols, such as, for example, with methanol, ethanol, octadecanol, 1,6-hexanediol;. 1,9-nonanediol, ethylene glycol, 1,2-propane-diol, diethylene glycol, thiodiethylene glycol, nepentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

1.11. Esters of β-(5-tert.-butyl-4-hydroxy-3-methylphenyl)propionic acid with a monohydric or polyhydric alcohols, such as for example, with methanol, ethanol, octadecanol, 1,6-hexanediol, 1,9-nonanediol, ethylene glycol, 1,2-propanediol, di-ethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2.]octane.

1.12. Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane, especially the tetrakis ester of pentaerythritol.

1.13. Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

3. Light-stabilisers 2.1. Esters of optionally substituted benzoic acid, e.g., 3,5-di-tert.-butyl-4-hydroxybenzoic acid, 2,4-di-tert.-butylphenyl ester of -octadecyl ester or 2-methyl-4,6-di-tert.-butylphenyl ester.

2.2. Sterically hindered amines e.g., 4-benzoyl-2,2,6,6-tetramethylpiperidine, 4-stearyloxy-2,2,6,6-tetramethyl-piperidine, bis-(2,2,6,6-tetramethylpiperidyl)-sebacate, bis-(1,2,2,6,6-pentamethylpiperidyl)sebacate, bis-(1,2,2,6,6-pentamethylpiperidyl)-2-n-butyl-2-(2-hydroxy-3,5-di-tert-butylbenzyl)malonate or 3-n-octyl-7,7,9,9-tetra-methyl-1,3,8-triazaspiro[4.5]decane-2,4-dione.

2.3. Oxalic acid diamides, e.g., 4,4'-di-octyloxy-oxanilide, 2,2'-di-octyloxy-5,5'-di-tert.-butyl-oxanilide, 2,2'-di-dodecycloxy-5,5'-di-tert.-butyl-oxanilide, 2-ethoxy-2'-ethyloxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixture of ortho- and para-methoxy- as well as of o- and p-ethoxy-di- substituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxy-phenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilizers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl)phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl)diphenylene-4,4'-bis-(phosphonite).

Other additives that can be incorporated in the stabilized compositions are thiosynergists, such as dilauryl thiodiproprionate, lubricants such as stearyl alcohol, fillers, asbestos, kaolin, talc, glass fibers, pigments, optical brighteners, flameproofing agents and antistatic agents.

This invention also pertains to a composition, stabilized against degradation, which comprises (a) a saturated polyolefin or mixture thereof, (b) a stabilizing amount of a stabilizer or mixture of stabilizers selected from the group consisting of the phenolic antioxidants, the hindered amine light stabilizers, the alkylated hydroxybenzoate light stabilizers, the ultraviolet light absorbers, the organic phosphorus compounds, the alkaline metal salts of fatty acids and the thiosynergists, and (c) a stabilizing amount of a hydroxylamine, or mixture of said hydroxylamines, of formula I.

The instant composition is stabilized against degradation and/or discoloration upon exposure to heating at elevated temperatures, to the combustion products of natural gas, to gamma irradiation or to prolonged storage at ambient temperature.

More particularly, the instant invention pertains to a stabilized composition wherein component (b) is a stabilizing amount of a phenolic antioxidant or mixture thereof in combination with a stabilizing amount of an alkaline metal salt of a fatty acid or mixture thereof.

The saturated polyolefins useful in the instant compositions are the polymers, derived from monoolefins, such as polyethylene, which can optionally be cross-linked, polypropylene, polyisobutylene, polybutene-1, poly-3-methylbutene-1 and polymethylpentene-1. Polyethylene may be for example medium density, high density or linear low density polyethylene.

Mixtures of the homopolymers cited above, for example mixtures of polypropylene and polyethylene, polypropylene and polybutene-1, or polypropylene and polyisobutylene and the like, may also be used.

Copolymers of monoolefins may also be used in the instant compositions, for example ethylene/propylene copolymers, propylene-butene-1 copolymers, propylene/octene-1 copolymers, ethylene/butene-1 copolymers, ethylene/octene-1 copolymers as well as ethylene/vinyl acetate copolymers.

The instant compositions particularly employ as the polyolefin component, polyethylene, polypropylene, polyisobutylene, poly(butene-1), poly(pentene-1), poly(3-methylbutene-1), poly(4-methyl-pentene-1) and various ethylene or propylene copolymers.

Especially preferred polyolefin substrates are polypropylene, low density polyethylene, medium density polyethylene, high density polyethylene, linear low density polyethylene, poly(butene-1), ethylene/vinyl acetate copolymer, ethylene/propylene copolymer and copolymers of ethylene or of propylene with other alpha olefins.

The most preferred polyolefin substrate is polypropylene, high density polyethylene, ethylene/propylene copolymer or a copolymer of ethylene or of propylene with another alpha olefin.

The phenolic antioxidants useful in the instant compositions enbrace a large family of compounds examples of which are given below.

Antioxidants

Simple 2,6-dialkylphenol, such as, for example, 2,6-di-tert.-butyl-4-methylphenol, 2-tert.-butyl-4,6-dimethylphenol, 2,6-di-tert.-butyl-4-methoxymethylphenol 2,6-dioctadecyl-4-methylphenol and 2,6-di-tert-butylphenol.

Derivatives of alkylated hydroquinones, such as for example, 2,5-di-tert-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl)phosphite, 3,5-di-tert.-butyl-4-hydroxyphenyl stearate and bis-(3,5-di-tert.-butyl-4-hydroxyphenyl)adipate.

Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)disulfide.

Alkylidene-bisphenols, such as, for example, 2,2'-methylene-bis-(6-tert.-butyl-4-methylphenol), 2,2'-methylene-bis-(6-tert.-4-ethylphenol), 4,4'-methylene-bis-(6-tert.-butyl-2-methylphenol), 4,4'-methylene-bis-(2,6-di-tert.-butylphenol), 2,6-di(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl)dithioterephthalate.

Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]]2,2-bis-(3,5-di-tert.-butyl-4-hydroxybenzyl)-malonate.

Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri(b 3,5-di-tert.-butyl-4-hydroxybenzyl)-phenol.

s-Triazine compounds, such as, for example, 2,4-bis-octylmercapto-6-(3,5-di-tert.-butyl-4-hydroxy-anilino)-s-triazine, 2-octylmercapto,4,6-bis-(3,5-di-tert.-butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenyl)-s-triazine, 2,4,6-tris-(3,5-di-tert-butyl-4-hydroxyphenylethyl)-s-triazine, 1,3,5-tris-(2,6-dimethyl-3-hydroxy-4-tert-butylbenzyl)isocyanurate and 1,3-5-tris-(3,5-di-tert.-butyl-4-hydroxybenzyl)isocyanurate.

Amides of β-(3,5-di-tert.-butyl-4-hydroxyphenyl)-propionic acid, such as, for example, 1,3,5-tris-(3,5-di-tert.-butyl-4-hydroxypheny-propionyl)-hexahydro-s-triazine and N,N'-di(3,5-di-tert.-butyl-4-hydroxyphenyl-propionyl)-hexamethylenediamine. N,N'-bis-β-(3,5-di-t-butyl-4-hydroxyphenyl)-propionylhydrazine.

Esters of β-(b 3,5-di-tert.-butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, triethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

Esters of β-(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

Esters of 3,5-di-tert.-butyl-4-hydroxyphenylacetic acid with monohydric or polyhydric alcohols, such as for example, with methanol, ethanol, octadecanol, 1,6-hexandiol, 1,9-monanediol, ethylene glycol, 1,2-propenediol, diethylene glycol, thio-diethylene glycol, neopentylglycol, pentaerythritol, 3-thia-undecanol, 3-thia-pentadecanol, trimethylhexanediol, trimethyloleth-ane, trimethylolpropane, tris-hydroxyethyl isocyanurate and 4-hydroxymethyl-1-phospha-2,6,7-trioxabicyclo[2,2,2]-octane, especially the tetrakis ester of pentaerythritol.

Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl4-tert-butyl-3-hydroxybenzyl-)isocyanurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octyl-thio)-s-triazine, N,N'-hexamethylene-bis(3,5-di-tert-butyl-4-hydroxyhydrocinnamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-tert-butyl-4-hydroxyhydrocinnamoyl)hydrazide, and N,N'-bis-[2-(3,5-di-tert-butyl-4-hydroxyhydrocinnamoyloxy)ethyl]oxamide.

A most preferred embodiment has as the phenolic antioxidant, neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol 2,2'-ethylidene-bis(4,6-di-tert-butyl-phenol).

When the instant compositions contain an alkaline metal salt of a fatty acid, such salts are the alkali metal, alkaline earth metal, zinc, cadmium or aluminum salts of the higher fatty acids for example calcium stearate, zinc stearate, magnesium behenate, sodium ricinoleate or potassium palmitate. Calcium stearate is particularly preferred.

When the instant compositions contain an organic phosphorus compound, such compounds may be for example, triphenyl phosphite, diphenylalkyl phosphites, phenyldialkyl phosphites, tri-(nonylphenyl)phosphite, trilauryl phosphite, trioctadecyl phosphite, di(isodecyloxy)-2,4,8,10-tetraoxa-3,9-diphospha-[5.5]-undecane and tri-(4-hydroxy-3,5-di-tert-butylphenyl)phosphite or similar phosphonites.

The organic phosphorus compound of particular interest is selected from the group consisting of tris(2,4-di-tert-butylphenyl)phosphite, 3,9-di(2,4-di-tert-butylphenoxy)-2,4,8,10-tetraoxa-3,9-diphospha[5.5]undecane, tris(p-nonylphenyl)phosphite, 3,9-distearyloxy-2,4,8,10-tetraoxa-3,9-diphospha[5.5]undecane, dilauryl phosphite, 3,9-di[2,6-di-tert-butyl-4-(2-(n-octadecyloxycarbonyl)ethyl)-phenoxy]-2,4,8,10-tetraoxa-3,9-diphospha[5.5]undecane and tetrakis(2,4-di-tert-butylphenyl) 4,4'-bis(diphenylene)phosphonite. Tris(2,4-di-tert-butylphenyl)phosphite is especially preferred.

When the instant compositions contain a thiosynergist, such thiosynergists may be for example dilauryl thiodiproionate, distearyl thiodipropionate or neopentanetetrayl tetrakis(3-dodecylthiopropionate). Distearyl thiodipropionate or dilauryl thiodipropionate is particularly preferred.

When the instant compositions contain a hindered amine light stabilizer, such hindered amines may for example be 4-benzoyl-2,2,6,6-tetramethylpiperidine, 4-stearyloxy-2,2,6,6-tetramethylpiperidine, bis-(2,2,6,6-tetramethylpiperidyl)sebacate or 3-n-octyl-7,7,9,9-tetramethyl-1,3,8-triaza-spiro[4.5]decane-2,4-dione.

The hindered amine light stabilizer of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxethyl)-2,2,6,6-tetramethyl-4-hydroxypiperidine and succinic acid, polycondensation product of 4,4'-hexamethylenebis(amino-2,2,6,6-tetramethylpiperidine) and 1,2-dibromoethane, polycondensation product of 2,4-dichloro-6-morpholino-s-triazine and 4,4'-hexamethylenebis(amino-2,2,6,6-tetramethylpiperidine), N,N'N"N'"-tetrakis[(4,6-bis(butyl-(2,2,6,6-tetramethyl-piperidin-4-yl)-amino-s-triazin-2-yl]-1,10-diamino-4,7-diazadecane, octamethylene bis(2,2,6,6-tetramethyl-piperidin-4-carboxylate) and 4,4'-ethylenebis(2,2,6,6-tetramethylpiperazin-3-one).

A most preferred embodiment has as the hindered amine light stabilizer bis(2,2,6,6-tetramethylpiperidin-4-yl)sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine) or N,N', N"N'"-tetrakis[(4,6-bis(butyl-(2,2,6,6-tetramethyl-yl-piperidin-4-yl)amino)-s-triazine-2-yl]-1,10-diamino-4,7-diazadecane.

When the instant compositions contain an ultraviolet light absorber, such light absorbers may include the 2H-benzotriazoles, the benzophenones, the oxanilides, the alpha-cyanocinnamates the substituted benzoate esters or the nickel salts of the O-alkyl hindered phenolic benzylphosphonates.

Examples of such ultraviolet light absorbers are seen below.

UV-Absorbers 2-(2'-Hydroxyphenyl)-benzotriazoles, e.g., the 5'-methyl-, 3,',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3', 5'-di-tert.-amyl-derivative.

2,4-bis-(2'-Hydroxyphenyl)-6-alkyl-s-triazines, e.g., the 6-ethyl-, 6-heptadecyl- or 6-undecyl-derivative.

2-Hydroxybenzophenones e.g., the 4-hydroxy-, 4-methoxy-, 4-octoxy-, 4-decyloxy-, 4-dodecyloxy-, 4-benzyloxy-, 4,2',4'-trihydroxy-, 2,2', 4,4'-tetrahydroxy- or 2'-hydroxy-4,4'-dimethoxy-derivative.

1,3-bis-(2'-Hydroxybenzoyl)-benzenes, e.g., 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxybenzoyl)-benzene.

Esters of optionally substituted benzoic acids, e.g., phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

Acrylates, e.g., α-cyano-β,β-diphenylacrylic acid-ethyl ester or isooctyl ester, α-carbomethoxy-cinnamic acid methyl ester, α-cyano-β-methyl-p-methoxy-cinnamic acid methyl ester or -butyl ester or N(β-carbomethoxyvinyl)-2-methyl-indoline.

Oxalic acid diamines, e.g., 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyloxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

Preferably the ultraviolet light absorber used in the instant compositions is 2-(2-hydroxy-5-methylphenyl)-2H-benzotriazole, 2-(2-hydroxy-3,5-di-tert-amylphenyl)-2H-benzotriazole, 2-[2-hydroxy-3,5-di-alpha,alpha-dimethylbenzyl)phenyl]-2H-benzotriazole, 2-(2-hydroxy-5-tert-octylphenyl)-2H-benzotriazole, 2-hydroxy-4-octyloxybenzophenone, nickel bis(O-ethyl 3,5-di-tert-butyl-4-hydroxybenzylphosphonate), 2,4-dihydroxybenzophenone, 2-(2-hydroxy-3-tert-butyl-5-methylphenyl)-2H-benzotriazole, nickel butylamine complex with 2,2'-thiobis(4-tert-butylphenol), 2-ethoxy-2'-ethyloxanilide or 2-ethoxy-2'-ethyl-5,5'-di-tert-butyloxanilide.

The stabilized polyolefin compositions of the instant invention may also contain other additives such as the pigments, colorants or dyes, light stabilizers such as metal deactivators, talc and other fillers, etc.

In general, the hydroxylamine stabilizers of this invention are employed from about 0.01 to about 5% by weight of the stabilized composition, although this will vary with the particular substrate and application. An advantageous range is from about 0.025 to about 2%, and especially 0.05 to about 1%.

The hydroxylamine compounds of this invention stabilize polyolefins especially during high temperature processing with relatively little change in color, even though the polymer may undergo a number of extrusions.

The instant stabilizers may readily be incorporated into the polyolefins by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polyolefin compositions of the invention may optionally also contain from about 0.01 to about 5%, preferably from about 0.025 to about 2%, and especially from about 0.1% to about 0.05%, by weight of various conventional additives, such as the following, or mixtures thereof:

The following may be mentioned as examples of further additives that can be used in the instant compositions.

Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)hydrazine, N-salicyloyl-N'-salicylalhydrazine, 3-salicyloyl-amino-1,2,4-triazole or N,N'-bis-salicyloyl-thiopropionic acid dihydrazide.

Nucleation agents, e.g., 4-tert.-butylbenzoic acid, adipic acid, diphenylacetic acid or substituted sorbitols such as 1,3; 2,4-dibenzylidenesorbitol.

Other additives that can be incorporated in the stabilized compositions are antiblocking agents, clarifiers, antiozonants, lubricants such as stearyl alcohol, fillers, carbon black, asbestos, kaolin, talc, glass fibers, pigments, optical brighteners, flameproofing agents and antisatic agents.

While the stabilizers of this invention may be conveniently incorporated by conventional techniques into polyolefins before the fabrication thereof into shaped articles, it is also possible to apply the instant stabilizers by a topical application to the finished articles. This is particularly useful with fiber applications where the instant stabilizers are applied topically to the fibers, for example, by way of a spin finish during the melt spinning process.

The following examples are presented for the purpose of illustration only and are not to be construed to limit the nature of scope of the instant invention in any manner whatsoever.

EXAMPLE 1

N,N-bis-(p-methoxycarbonylbenzyl)hydroxylamine

A solution of 19.5 grams of alpha-bromo-p-toluoyl chloride in 100 ml of methylene chloride is added to a solution of 15.7 ml of triethylamine in 100 ml of methanol. The reaction mixture is stirred overnight at room temperature and then concentrated. The residue is dissolved in ether, washed with water and the ether evaporated to give the intermediate p-methoxycarbonylbenzyl bromide.

To a stirred suspension of 1.11 grams of hydroxylamine hydrochloride and 6.78 grams of anhydrous sodium carbonate in 20 ml of dry N,N-dimethylformamide (DMF) is added a solution of 7.49 grams of p-methoxycarbonylbenzyl bromide in 30 ml of dry DMF. The mixture is stirred at ambient temperature for 24 hours. Insoluble material present is removed by filtration and the filtrate is concentrated. The above-named product is obtained from the resulting residue by preparative liquid chromatography as 2.8 grams of a white solid, melting at 129°–131° C.

Analysis: Calcd for $C_{18}H_{19}NO_5$: C, 65.6; H, 5.8; N, 4.3. Found: C, 65.3; H, 5.7; N, 4.3.

EXAMPLE 2

N,N-Bis(p-n-octadecyloxycarbonylbenzyl)hydroxylamine

Using the procedure of Example 1, 19.5 grams of alpha-bromo-p-toluoyl chloride, 20.29 grams of n-octadecanol and 15.7 ml of triethylamine yields 15.0 grams of the corresponding n-octadecyl ester. Said ester is reacted with 1.11 grams of hydroxylamine hydrochloride and 6.78 grams of anhydrous sodium carbonate in dry DMF by the method of Example 1 to give the above-named product as a white solid, melting at 84°–86° C.

Analysis: Calcd for $C_{52}H_{87}NO_5$: C, 77.5; H, 10.9; N, 1.7. Found: C, 77.8; H, 10.7; N, 1.9.

EXAMPLE 3

1,6-Hexamethylene Bis(p-N-benzyl-N-hydroxyaminomethylbenzoate)

1,6-Hexamethylene bis(p-alpha-bromomethylbenzoate) is made following the procedure of Example 1 by reacting 16.30 grams of p-alpha-bromo-p-toluoyl chloride, 4.13 grams of 1,6-hexamethylene glycol and 9.73 ml of triethylamine.

Four grams of the bis-hexamethylene ester is reacted with 1.92 grams of N-benzylhydroxylamine in 26 ml of dry DMF in the presence of 1.66 grams of anhydrous sodium carbonate. After stirring at room temperature for 48 hours, the above-named product is isolated and purified by the method of Example 1 to give 4.0 grams of a white solid, melting at 113°–115° C.

Analysis: Calcd for $C_{36}H_{40}N_2O_6$: C, 72.5; H, 6.8; N, 4.7. Found: C, 72.5; H, 6.6; N, 4.5.

EXAMPLE 4

Neopentanetetrayl Tetrakis(p-N-benzyl-N-hydroxyaminomethylbenzoate)

To a stirred mixture of 13.62 grams of pentaerythritol and 70 ml of triethylamine in 100 ml of methylene chloride is added a solution of 64.9 grams of p-toluoyl chloride in 150 ml of methylene chloride. After stirring at room temperature for 8 hours and under reflux for 2 hours more, the reaction mixture is concentrated and the residue triturated with ethanol to give 54.88 grams of neopentanetetrayl tetrakis(p-methylbenzoate).

A mixture of the intermediate ester prepared above, 66.5 grams of N-bromosuccinimide and 5 grams of benzoyl peroxide in 500 ml of carbon tetrachloride is irradiated for 1 hour under a sun lamp. Removal of the succinimide formed by filtration followed by evaporation under reduced pressure leaves 81.5 grams of the corresponding neopentanetetrayl tetrakis(p-alpha-bromomethylbenzoate).

9.38 Grams of the brominated ester prepared above is reacted with 5.0 grams of N-benzylhydroxylamine in 30 ml of dry DMF in the presence of 4.30 grams of anhydrous sodium carbonate. The above named compound is isolated and purified by the method of Example 1.

EXAMPLE 5

N,N-Bis(p-carboxybenzyl)hydroxylamine

When N,N-bis(p-methoxycarbonylbenzyl)hydroxylamine, prepared in Example 1, is dissolved in an organic solvent and saponified with an aqueous sodium hydroxide solution, th above-named free acid compound is obtained after acidification with a mineral acid.

EXAMPLE 6

N,N-Bis(p-carboxybenzyl)hydroxylamine Dipotassium Monohydrate Salt

A slurry of 6.58 grams of N,N-bis(p-methoxycarbonylbenzyl)hydroxylamine, prepared in Example 1, and 5.13 grams of potassium trimethylsilanoate in 50 ml of tetrahydrofuran is stirred for 5 hours at room temperature. The insoluble residue which results in removed by filtration and is triturated with 50 ml of isopropanol to give 5.9 grams of the above-named compound as a white solid, melting at over 250° C.

Analysis: Calcd for $C_{16}H_{13}NO_5K_2H_2O$: C, 48.6; H, 3.8; N, 3.5. Found: C, 49.0; H, 3.5; N, 3.6.

EXAMPLE 7

Processing Stability of Polypropylene at 500° F. (260° C.)

The base formulation comprises 100 parts of unstabilized polypropylene (Profax 6501, Hercules) with 0.10 parts of calcium stearate. The test stabilizers are solvent blended onto the polypropylene from solution in methylene chloride. After removal of the solvent by evaporation under reduced pressure, the stabilized resin formulation is extruded at 100 rpm from a 1 inch (2.54 cm) diameter extruder under the following extruder conditions:

| Extruder Location | Temperature °F. | °C. |
|---|---|---|
| Cylinder #1 | 450 | 232 |
| Cylinder #2 | 475 | 246 |
| Cylinder #3 | 500 | 260 |
| Gate #1 | 500 | 260 |
| Gate #2 | 500 | 260 |
| Gate #3 | 500 | 260 |

After each of the first, third and fifth extrusions, resin pellets are compression molded into 125 mil (3.2 mm) thick plaques at 380° F. (193° C.) and specimen yellowness index (YI) is determined according to ASTM D1925. Low YI values indicate less yellowing.

Results are seen in Table I.

It is clear from the data in Table I that the presence of the ester substituted benzylhydroxylamine in the polypropylene composition containing a phenolic antioxidant essentially eliminates all color formation associated with the presence of the phenolic antioxidant while the phenolic antioxidant still stabilizes the polypropylene effectively from degradation after heating.

TABLE I

| | Conc. Stabilizer | Yellowness Index Color After Extrusion | | |
|---|---|---|---|---|
| Stabilizer* | % by wt. | 1 | 3 | 5 |
| Base formulation | — | 4.4 | 6.6 | 8.0 |
| Antioxidant A | 0.1 | 7.1 | 11.0 | 12.0 |
| Antioxidant A plus Compound | 0.1 | | | |
| of Example 1 | 0.05 | 4.1 | 6.7 | 7.5 |
| of Example 2 | 0.05 | 4.6 | 5.6 | 6.2 |

Processing stability of polypropylene at 500° F. (260° C.)

*Antioxidant A = neopentanetetrayl tetrakis(3,5-di-tert-butyl-4-hydroxyhydrocinnamate)

The instant compounds are significantly effective as color improvers in the polypropylene compositions containing a phenolic antioxidant. Also, they prevent the discoloration of polypropylene compositions, containing a hindered amine light stabilizer or in combination with a phenolic antioxidant or combination of phenolic antioxidant and an organic phosphite, in respect to gas fading.

EXAMPLE 8

The instant compounds exhibit resistance to loss through volatilization when held at high temperature as is encountered during the processing of polyolefins such as polypropylene or polyethylene.

This is evidenced by inspection of thermal gravimetric analyzer scans from room temperature to 500° C. at a rate of 10°(C.)/minute, under a flow of 100 ml nitrogen/minute at 80% suppression which shows as is seen in the table below that the instant compounds are relatively non-volatile and thus would resist loss by volatilization when used as process stabilizers for polyolefins.

| Compound of | Temperature (°C.) at Percent Weight Loss | | |
|---|---|---|---|
| | 1% | 10% | 50% |
| Example 2 | 275 | 310 | 380 |
| Example 3 | 195 | 235 | 390 |

EXAMPLE 9

Resistance to Gas Fading of Polypropylene Fibers

The base formulation comprises 100 parts of unstabilized polypropylene (Profax 6501, Hercules) with 0.10 parts of calcium stearate. Various test stabilizers are solvent blended onto the polypropylene and extruded (one extrusion) as described in Example 7 and pelletized.

The stabilized resin pellets obtained are spun into fibers at 500° F. (260° C.) and a visual color rating number is assigned before exposure to gas fading at 140° F. (60° C.) and after 2, 6, 24 and 48 hours of exposure. Lower numbers indicate less yellowing and less color. The gas fading procedure is carried out in an AATCC gas fume chamber (Drum Model No. 8727) according to the standard procedure of AATCC Test Method 23, Colorfastness to Burnt Gas Fumes.

The results are given in Table II.

TABLE II

Discoloration Resistance of Stabilized Polypropylene Fibers to Gas Fading

| Stabilizer* | Conc. Stabilizer % by wt. | Visual Color Rating After Hours Exposure To Gas Fading at 140° F. (60° C.) | | | | |
|---|---|---|---|---|---|---|
| | | 0 | 2 | 6 | 24 | 48 |
| Base formulation plus | — | | | | | |
| Antioxidant A | 0.05 | 0 | 2 | 4 | 5 | 5 |
| Light stabilizer a | 0.25 | | | | | |
| Phosphorus I | 0.05 | | | | | |
| plus compound | | | | | | |
| of Example 2 | 0.25 | 1 | 1 | 1 | 3 | 5 |
| of Example 3 | 0.25 | 1 | 1 | 1 | 2 | 2 |

*Light stabilizer a = polycondensation product of 2,4-di-chloro-6-tert-octylamino-s-triazine and 4,4'-hexamethylenebis(amino-2,2,6,6-tetramethylpiperidine)
Antioxidant A = neopentanetetrayl tetrakis(3,5-di-tert-butyl-4-hydroxyhydrocinnamate)
Phosphorus I = tris(2,4-di-tert-butylphenyl)phosphite From the results given in Table II, it is seen that the instant compounds prevent the discoloration of polypropylene fibers, having various other stabilizers present, in respect to gas fading. These include polypropylene containing a hindered amine light stabilizer in combination with a phenolic antioxidant, and an organic phosphite.

What is claimed is:

1. A compound of formula I

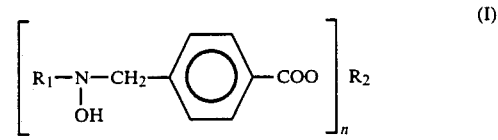

wherein
n is 1, 2, 3 or 4,
$R_1$ is alkyl of 1 to 36 carbon atoms, cycloalkyl of 5 to 12 carbon atoms, aralkyl of 7 to 9 carbon atoms or said aralkyl substituted by alkyl of 1 to 36 carbon atoms or by —$COOT_1$ where $T_1$ has the same meaning as $R_1$ or is hydrogen or an alkali metal or ammonium salt,
when n is 1, $R_2$ has the same meaning as $R_1$ or is hydrogen or an alkali metal or ammonium salt,
when n is 2, $R_2$ is alkylene of 2 to 12 carbon atoms, cycloalkylene of 6 to 10 carbon atoms, arylene of 6 to 10 carbon atoms, alkylenearylenealkylene of 8 to 10 carbon atoms or

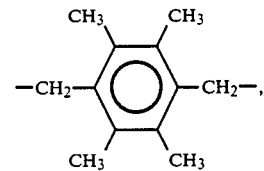

or $R_2$ is an alkaline earth salt,
when n is 3, $R_2$ is alkanetrityl of 3 to 6 carbon atoms, or

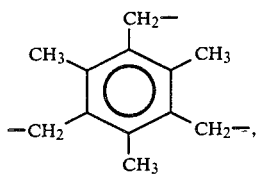

or when n is 4, R$_2$ is alkanetetrayl of 4 to 6 carbon atoms.

2. A compound according to claim 1 wherein n is 1 and R$_2$ is alkyl of 1 to 18 carbon atoms.

3. A compound according to claim 1 wherein n is 2 and R$_2$ is alkylene of 2 to 8 carbon atoms.

4. A compound according to claim 1 wherein n is 4 and R$_2$ is (—CH$_2$)$_2$C(CH$_2$—)$_2$ or 1,2,3,4-butanetetrayl.

5. A compound according to claim 1 wherein R$_1$ is benzyl or benzyl substituted by —COOT$_1$ where T$_1$ is defined in claim 1.

6. The compound according to claim 1 which is N,N-bis-(p-methoxycarbonylbenzyl)hydroxylamine.

7. The compound according to claim 1 which is N,N-bis-(p-n-octadecyloxycarbonylbenzyl)hydroxylamine.

8. The compound according to claim 1 which is 1,6-hexamethylene bis-(p-N-benzyl-N-hydroxyaminomethylbenzoate).

9. The compound according to claim 1 which is neopentanetetrayl tetrakis-(p-N-benzyl-N-hydroxyaminomethylbenzoate).

10. The compound according to claim 1 which is N,N-bis(p-carboxybenzyl)hydroxylamine.

11. The compound according to claim 1 which is N,N-bis(p-carboxybenzyl)hydroxylamine dipotassium monohydrate salt 12. A composition, stabilized against degradation, which comprises
(a) a saturated polyolefin or mixture thereof,
(b) a stabilizing amount of a stabilizer or mixture of stabilizers selected from the group consisting of the phenolic antioxidants, the hindered amine light stabilizers, the alkylated hydroxybenzoate light stabilizers, the ultraviolet light absorbers, the organic phosphorus compounds, the alkaline metal salts of fatty acids and the thiosynergists, and
(c) a stabilizing amount of a compound of formula I

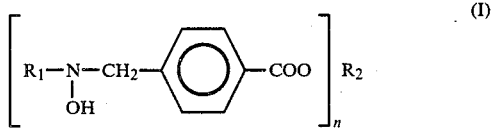

wherein
n is 1, 2, 3 or 4,
R$_1$ is alkyl of 1 to 36 carbon atoms, cycloalkyl of 5 to 12 carbon atoms, aralkyl of 7 to 9 carbon atoms or said aralkyl substituted by alkyl of 1 to 36 carbon atoms or by —COOT$_1$ where T$_1$ has the same meaning as R$_1$ or hydrogen or an alkali metal or ammonium salt,
when n is 1, R$_2$ has the same meaning as R$_1$ or hydrogen or an alkali metal or ammonium salt,
when n is 2, R$_2$ is alkylene of 2 to 12 carbon atoms, cycloalkylene of 6 to 10 carbon atoms, arylene of 6 to 10 carbon atoms, alkylenearylenealkylene of 8 to 10 carbon atoms or

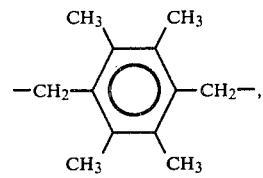

or R$_2$ is an alkaline earth salt,
when n is 3, R$_2$ is alkanetriyl of 3 to 6 carbon atoms, or

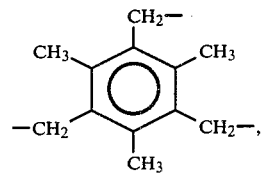

or when n is 4, R$_2$ is alkanetetrayl of 4 to 6 carbon atoms.

13. A composition according to claim 12 wherein component (a) is a polyolefin which is homopolymer or copolymer of an alpha-olefin.

14. A composition according to claim 13 wherein the polyolefin is selected from the group consisting of polypropylene, low density polyethylene, medium density polyethylene, high density polyethylene, linear low density polyethylene, poly(butene-1), ethylene/vinyl acetate copolymer, ethylene/propylene copolymer, and copolymers of ethylene or of propylene with other alpha-olefins.

15. A composition according to claim 14 wherein the polyolefin is polypropylene, high density polyethylene, ethylene/propylene copolymer or a copolymer of ethylene or of propylene with another alpha-olefin.

16. A composition according to claim 12 wherein component (c) is a compound of formula I where n is 2 and R$_2$ is alkylene of 2 to 8 carbon atoms.

17. A composition according to claim 12 wherein component (c) is 1,6-hexamethylene bis(p-N-benzyl-N-hydroxyaminomethylbenzoate).

18. A composition according to claim 12 wherein component (b) is an alkaline metal salt of fatty acid.

19. A composition according to claim 18 wherein the alkaline metal salt is calcium stearate, zinc stearate, magnesium gehenate, sodium ricinoleate or potassium palmitate.

20. A composition according to claim 19 wherein the alkaline metal salt is calcium stearate.

21. A composition according to claim 12 wherein componenet (b) also contains a phenolic antioxidant.

22. A composition according to claim 21 wherein the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3-tris-(2-methyl-4-hydroxy-5-tert-butylphenyl)butane, 1,3,5-tris[2-(3,5-di-tert-butyl-4-hydroxyhydrocinnamoyloxy)-ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamcyl)-hydrazide, and N,N'-bis[2-(3,5-tert-butyl-4-hydroxyhydroxocinnamoyloxy)ethyl]oxamide.

23. A composition according to claim 22 wherein the phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

* * * * *